(12) United States Patent
Herron

(10) Patent No.: US 10,065,065 B2
(45) Date of Patent: Sep. 4, 2018

(54) EXERCISE SUIT WITH INTEGRATED WEIGHTS

(71) Applicant: Derrick Herron, Orlando, FL (US)

(72) Inventor: Derrick Herron, Orlando, FL (US)

( * ) Notice: Subject to any disclaimer, the term of this patent is extended or adjusted under 35 U.S.C. 154(b) by 0 days.

(21) Appl. No.: 15/136,338

(22) Filed: Apr. 22, 2016

(65) Prior Publication Data

US 2017/0304670 A1 Oct. 26, 2017

(51) Int. Cl.
| | |
|---|---|
| *A61B 5/02* | (2006.01) |
| *A63B 21/065* | (2006.01) |
| *A63B 21/06* | (2006.01) |
| *A61B 5/024* | (2006.01) |
| *A61B 5/00* | (2006.01) |

(52) U.S. Cl.
CPC ........ *A63B 21/065* (2013.01); *A61B 5/02438* (2013.01); *A61B 5/6801* (2013.01); *A61B 5/742* (2013.01); *A61B 5/7405* (2013.01); *A61B 5/746* (2013.01); *A63B 21/0603* (2013.01); *A61B 2560/0487* (2013.01); *A63B 2220/62* (2013.01); *A63B 2230/04* (2013.01)

(58) Field of Classification Search
CPC .............. A63B 21/065; A63B 21/0603; A63B 2220/62; A63B 2230/04; A61B 5/02438; A61B 5/6801; A61B 5/7405; A61B 5/742; A61B 5/746; A61B 2560/0487
See application file for complete search history.

(56) References Cited

U.S. PATENT DOCUMENTS

| | | | | |
|---|---|---|---|---|
| 4,384,369 | A | * 5/1983 | Prince | A63B 21/065 2/227 |
| 5,048,125 | A | * 9/1991 | Libertini | A63B 21/065 2/79 |
| 2005/0054940 | A1* | 3/2005 | Almen | A61B 5/02405 600/509 |
| 2007/0276270 | A1* | 11/2007 | Tran | A61B 5/0022 600/508 |
| 2014/0200118 | A1 | 7/2014 | Lathen | |

* cited by examiner

*Primary Examiner* — George Manuel
(74) *Attorney, Agent, or Firm* — Jason T. Daniel, Esq.; Daniel Law Offices, P.A.

(57) ABSTRACT

An exercise suit with integrated weights includes a shirt portion and a pants portion that are constructed from a lightweight elastomeric material. A plurality of soft weights are disposed along the shirt and pants portions at locations adjacent to the major muscle groups of the suit wearer. Each of the weights can be permanently secured along the inside facing surface of the shirt and pants, and conform to the shape and movement of the suit wearer. The suit also includes a fitness monitor having a heartbeat sensor, timer and display.

11 Claims, 8 Drawing Sheets

EXERCISE SUIT WITH INTEGRATED WEIGHTS

TECHNICAL FIELD

The present invention relates generally to the field of physical fitness, and more particularly to exercise garments having integrated weights.

BACKGROUND

The statements in this section merely provide background information related to the present disclosure and may not constitute prior art.

Proper diet and regular exercise are among the best ways to ensure a long and healthy life. As such, there are thousands of fitness centers across the country that assist members in performing various forms of exercise such as running, cycling, aerobics, sports, weight training and swimming, for example.

To this end, the predominant type of exercise equipment found in any fitness center and/or home gym typically includes some type of weightlifting and/or resistance training system. When performing weight training, users stress their muscles which, over time, cause the body to increase the overall muscle content to accommodate the users demand. Additionally, higher level athletes often combine this weight training with other forms of exercise such as aerobics, for example. To this end, many athletes routinely utilize ankle weights, wrist weights and other such devices while running as a means to increase the intensity of the aerobic workout.

Although useful, these forms of wearable weights have heretofore been limited to bulky items that must be strapped onto the arms and/or legs of the user, thereby reducing the ability of the user to perform other tasks. Moreover, although there have been attempts to introduce whole-body suits containing externally located weights, these devices also suffer from many drawbacks, as the weights are typically large rigid members that do not flex with the movements of the user and often make inadvertent contact with external objects causing damage to the same.

Accordingly, it would be beneficial to provide weighted exercise garments that incorporate a plurality of strategically located weights within the body of the garment in a manner that allows a user to experience a full body workout while performing any type of activity, and without suffering from the drawbacks of the above noted devices.

SUMMARY OF THE INVENTION

The present invention is directed to an exercise suit with integrated weights. One embodiment of the present invention can include a shirt portion and a pants portion that are constructed from a lightweight elastomeric material which can be worn as an outer garment or as an undergarment. A plurality of soft weights can be disposed along each of the shirt and pants at locations adjacent to the major muscle groups of the suit wearer.

In one embodiment, the weights can be permanently secured along the inside facing surface of the shirt and pants, and are configured to conform to the shape and movement of the suit wearer. Another embodiment of the present invention can include a fitness monitor which can be integrated into the suit and can function to detect the heartbeat of the suit wearer.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

Figure 1A:
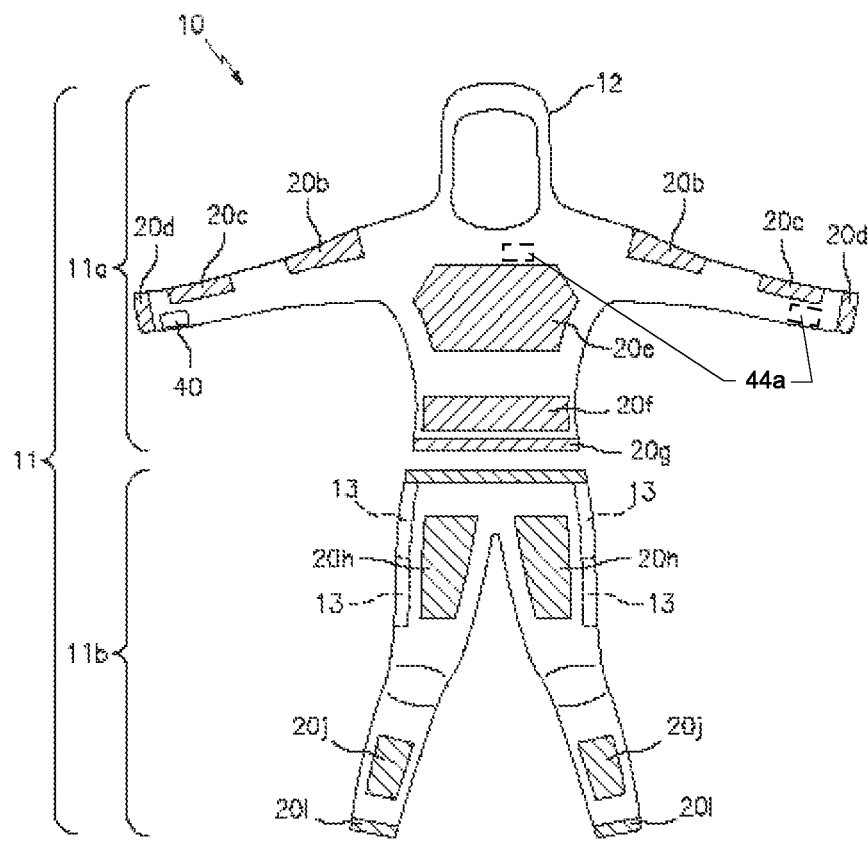
FIG. 1A is a front side view of an exercise suit with integrated weights that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1A.

Figure 1B:
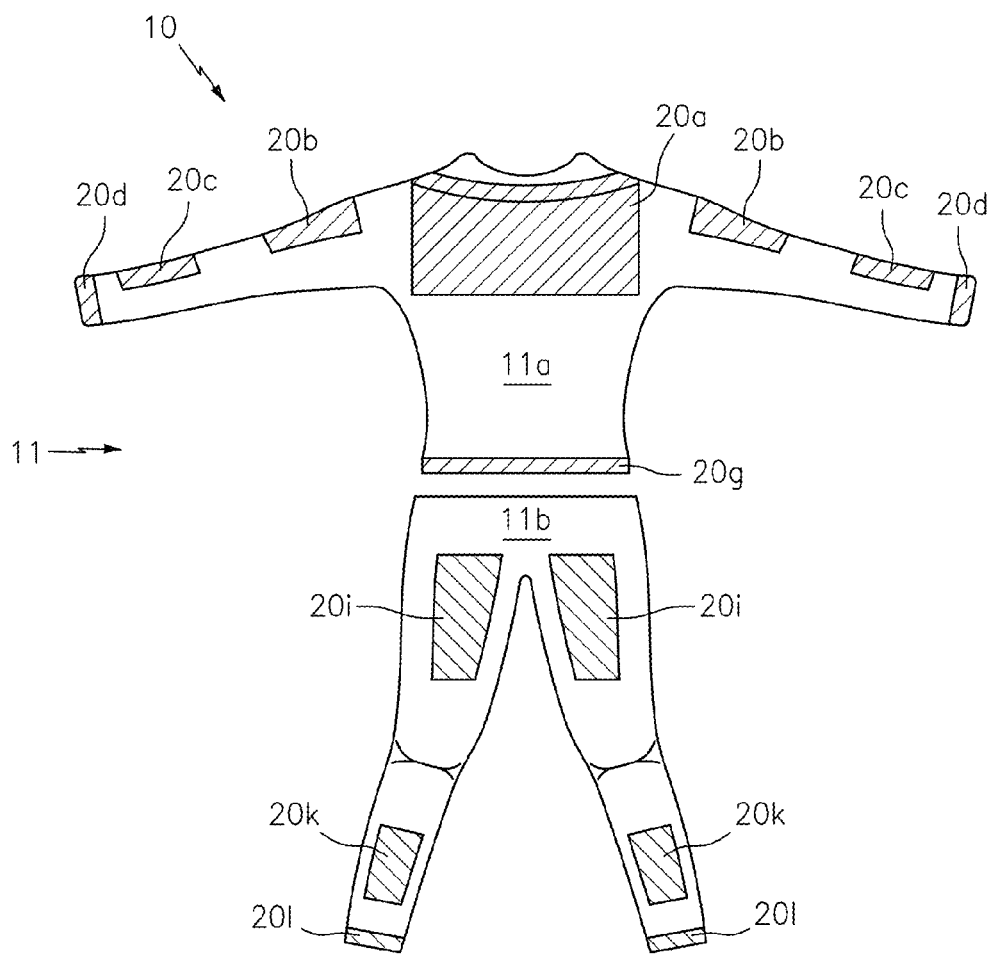
FIG. 1B is a back side view of an exercise suit with integrated weights, in accordance with one embodiment of the invention.

FIGS. 1A and 1B illustrate front and back side views of one embodiment of an exercise suit with integrated weights 10 that are useful for understanding the inventive concepts disclosed herein. As shown, the suit 10 can include a shirt member 11a, and a pants member 11b, referred to hereinafter collectively as 11, that are embedded with a plurality of internally located weights 20. In various embodiments, a fitness monitor 40 can be embedded within the suit to monitor the health and activities of the wearer.

In the present embodiment, the main body 11 also includes a hood portion 12 that is secured along the neckline of the shirt and functions to cover the head of the user. Additionally, a plurality of pockets 13 are disposed along the inside surface of the legs of the pants member 11b. Each of these pockets can function to receive additional weights 20 at the discretion of the user.

The main body 11 can be preferably constructed from a generally lightweight, breathable and elastomeric material such as spandex, for example. Construction of the clothing from such a material ensures a tight fitting garment against the skin of the wearer, and prevents movement of the same when the user perspires. Moreover, such materials include excellent tensile strength, and are extremely thin, thereby allowing the suit 10 to be worn as an undergarment beneath clothing such as traditional shorts or shirts, for example. Of course, any number of other materials including wicking fabrics such as high tech polyester, for example, that actively draws moisture and odors away from the body are also contemplated.

As shown, a plurality of weights referred to collectively at 20 can be secured along the inside facing surface of the main body 11 at specific locations to maximize the major muscle groups of the users' body. In the preferred embodiment, the shirt member 11a of the suit 10 can include an upper back/shoulder weight 20a, bicep weights 20b, triceps weights 20c, wrist weights 20d, a chest weight 20e (males only), an abdomen weight 20f and a waist weight 20g. Likewise, the pants member 11b of the suit 10 can include front thigh weights 20h, rear thigh weights 20i, front calf weights 20j, rear calf weights 20k and ankle weights 20l.

Although described above with respect to particular weights at designated locations, this is for illustrative purposes only, as such, other embodiments are contemplated where additional weights are included at other locations and/or not all of the above described weights are included within a particular suit.

In one exemplary embodiment, the suit 10 can be configured to apply a total weight of 100 pounds onto the major muscle groups of a user. As such, Table 1 outlines one possible distribution of the weights that would be suitable for an adult male athlete.

TABLE 1

| Location of weight(s) | number of weights | individual weight (lbs) | combined weight (lbs) |
|---|---|---|---|
| 20d-wrists | 2 | 1.25 | 2.5 |
| 20c-triceps | 2 | 2.5 | 5 |
| 20b-biceps | 2 | 2.5 | 5 |
| 20a-back | 1 | 10 | 10 |
| 20e-chest | 1 | 10 | 10 |
| 20f-abdomen | 1 | 10 | 10 |
| 20g-waist | 1 | 5 | 5 |
| 20h-front thigh | 2 | 5 | 10 |
| 20i-rear thigh | 2 | 5 | 10 |
| 20j-shin | 2 | 2.5 | 5 |
| 20k-rear calf | 2 | 2.5 | 5 |
| 20l-ankle | 2 | 1.25 | 2.5 |
| 13-pocket | 4 | 5 | 20 |
| | | Total weight | 100 |

Of course, the overall weight of the suit 10 and/or the specific weight of each element 20 can vary based on the fitness level, age, size and/or gender of the anticipated user of the suit. As such, suits employing a total weight of between 20 pounds and 200 pounds are fully contemplated.

Figure 2:
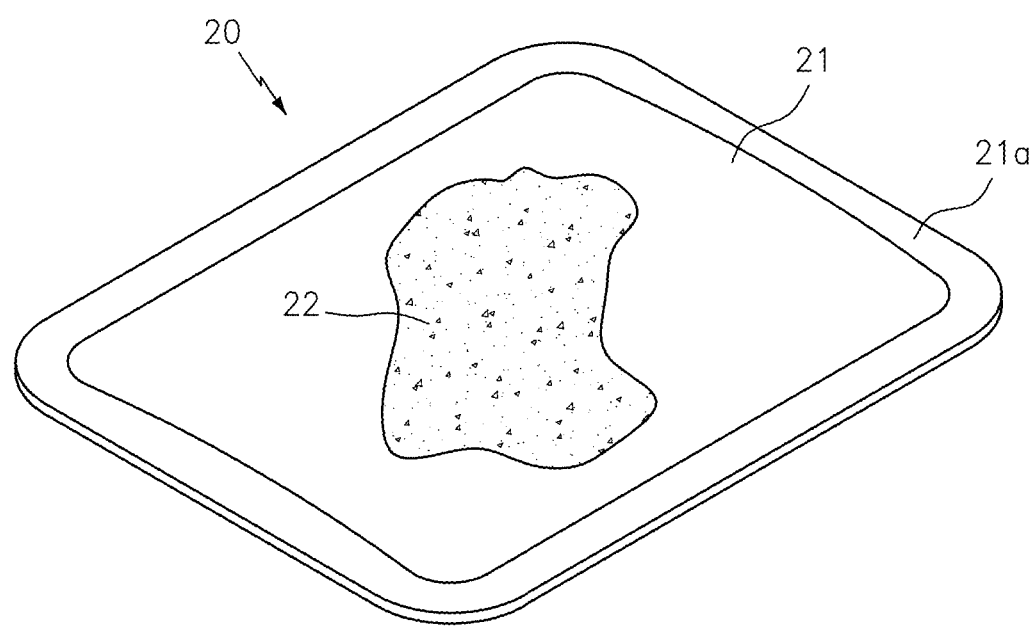
FIG. 2 is a perspective view of an exemplary weight, in accordance with one embodiment of the invention.

FIG. 2 illustrates one embodiment of one of the weights 20 that can be integrated into the suit 10. As shown, the weight 20 can preferably include a non-rigid, malleable member comprising a strong polyester or nylon bag 21 that is filled with sand, graphite beads, and/or other such weighted elements 22, for example.

As shown, the bag can include edging 21a along the outer periphery so as to allow the weights to be permanently affixed to the fabric of the main body 11. As described herein, any number of suitable materials and methodologies can be utilized to secure the weights to the identified portions of the suit body. Several nonlimiting examples include permanent sealers such as glue, adhesive tape, or commercial grade nylon stitching, for example.

The inclusion of malleable weights 20 allows the shape of each weight to conform to the body of the user and also will not cause damage to external items if contact is made. For example, if a user is wearing the exercise suit 10 beneath clothing such as a business suit, for example, the thin main body material 11 combined with the resilient nature of the weights 20 will not present a visible indication that the suit 10 is being worn as an undergarment. Moreover, while the user is performing routine tasks such as reaching for a glass of water, for example, accidental contact between the wrist weight 20d, and the fragile glass will not cause the same to shatter, owing to the resilient nature of the weight 20.

Accordingly, the above described suit 10 functions to allow a user to exercise the major muscle groups of their body at all times in a novel manner that does not affect other day to day activities.

Figure 3A:
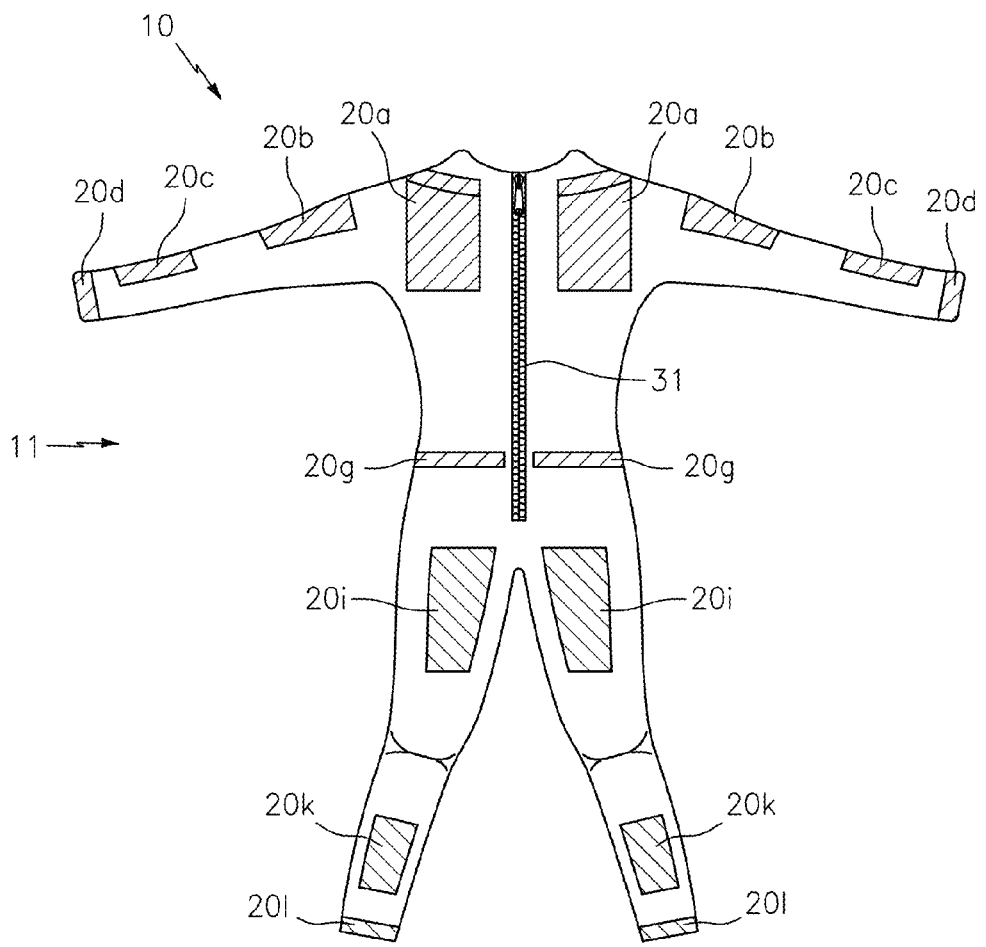
FIG. 3A is a back side view of the exercise suit with integrated weights, in accordance with another embodiment of the invention.

Although described above with respect to separate elements 11a and 11b, other embodiments are also contemplated. To this end, FIG. 3A illustrates another embodiment of the suit 10 having a main body 11' wherein the shirt and pants members 11a and 11b include a unitary construction. As shown, a zipper 31 or other such mechanism can also be provided to facilitating entry by a user.

Figure 3B:
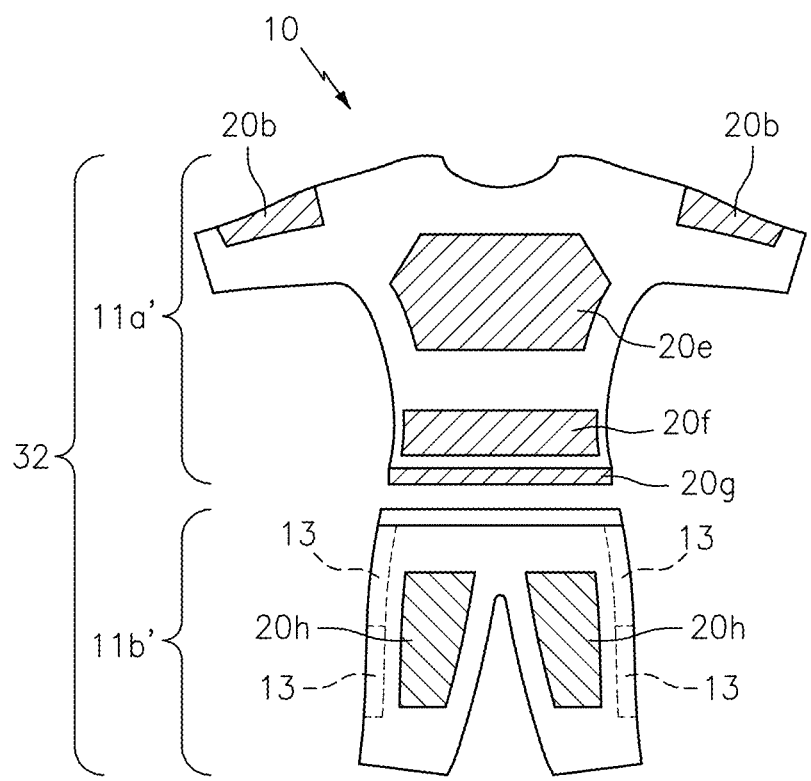
FIG. 3B is a front side view of the exercise suit with integrated weights, in accordance with another embodiment of the invention.
Figure 3C:
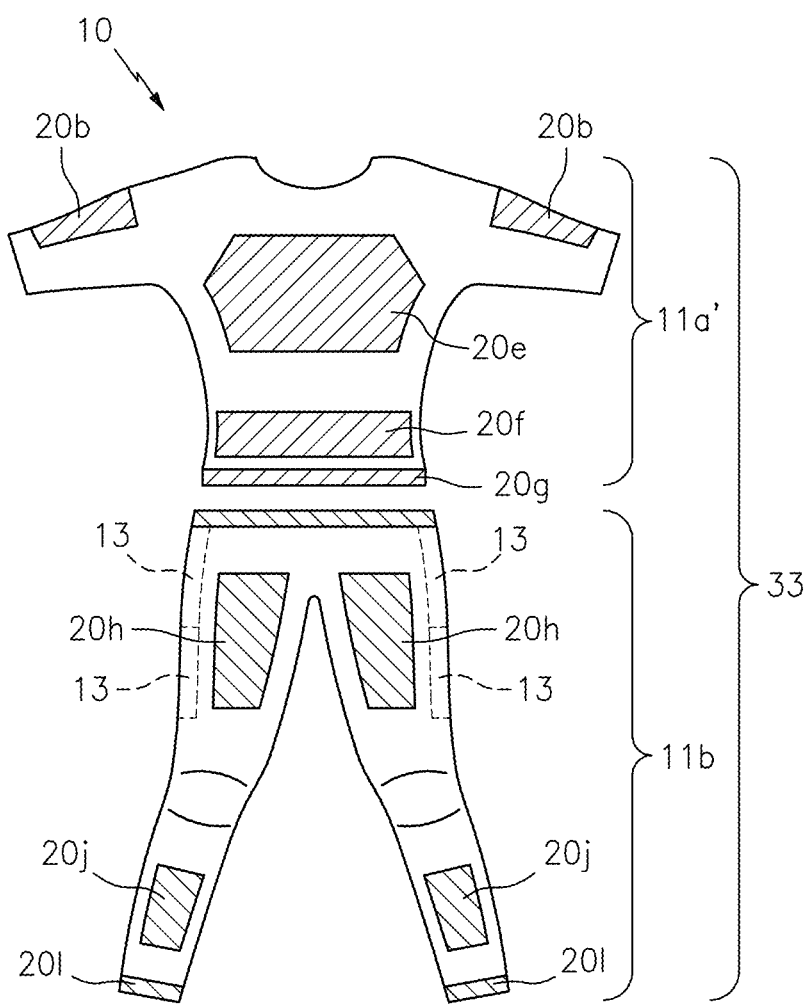
FIG. 3C is another front side view of the exercise suit with integrated weights, in accordance with another embodiment of the invention.
Figure 3D:
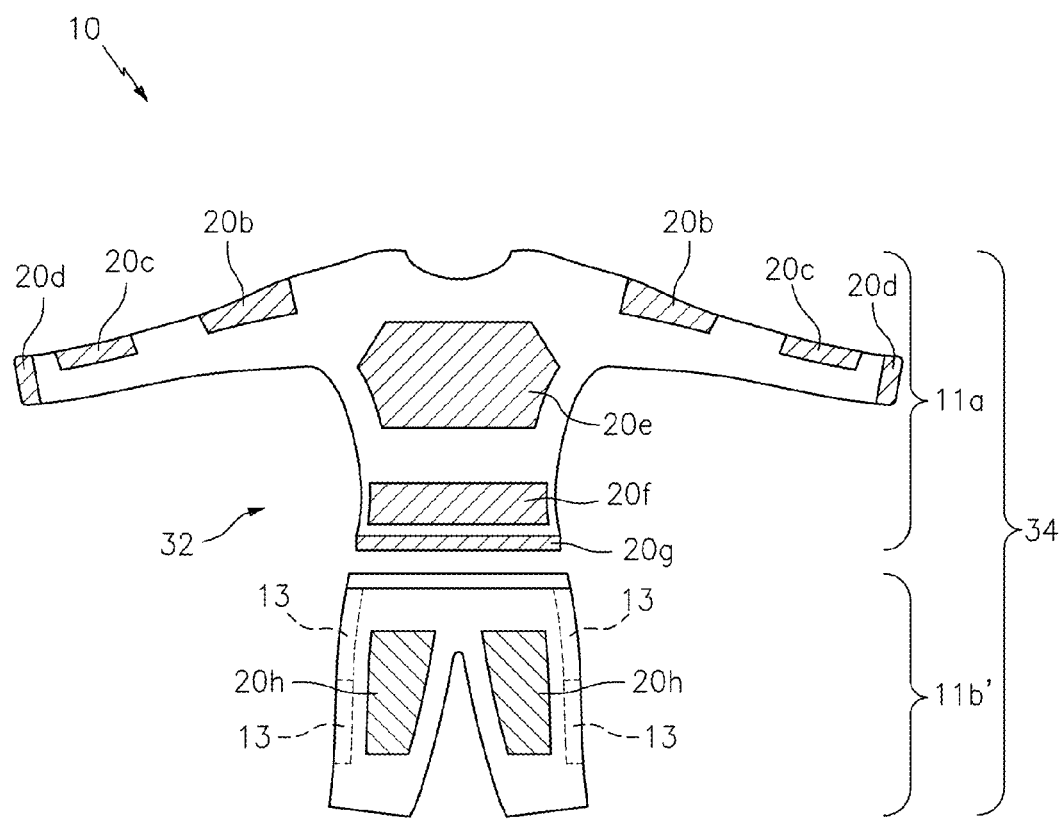
FIG. 3D is another front side view of the exercise suit with integrated weights, in accordance with another embodiment of the invention.

Of course, the main body is not to be construed as limiting to long sleeve shirt and full length pants, as any combination of these elements are also contemplated. To this end, FIG. 3B illustrates another embodiment of the suit 10 that further includes main body 32 having a short sleeve shirt member 11a' and short pants member 11b'. FIG. 3C illustrates another embodiment of the suit 10 that further includes main body 33 having a short sleeve shirt member 11a' and long pants member 11b. FIG. 3D illustrates another embodiment of the suit 10 that further includes main body 34 having a long sleeve shirt member 11a and short pants member 11b'.

In either instance, the suit 10 can be manufactured to fit men, women and children of any shape or size, and can include an unlimited number of decorative elements such as various colors, markings, words, shapes, symbols, logos, designs, texturing of materials, patterns, and/or images, for example. These elements can be secured onto and/or into the main body in accordance with known techniques so as to be flush with the surface of the main body or can be recessed, raised and/or protruding outward from the main body so as to give a three dimensional effect.

Figure 4:
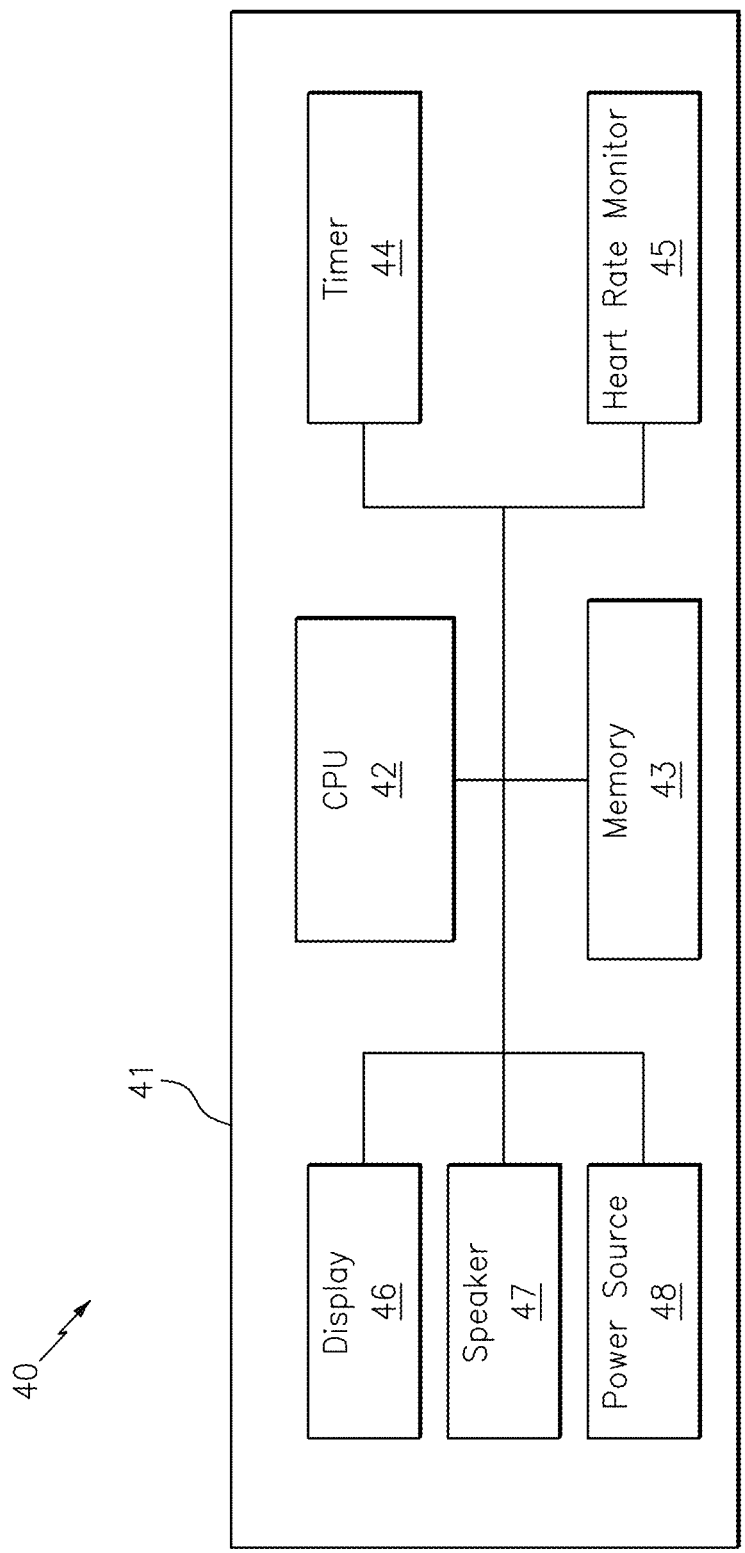
FIG. 4 is a schematic diagram of the fitness monitor of the exercise suit with integrated weights, in accordance with one embodiment of the invention.

FIG. 4 is a simplistic schematic diagram of the fitness monitor 40, which can be provided with the suit 10. In one embodiment, the fitness monitor 40 can include an outer shell/body 41 having a processor 42 that is conventionally connected to an internal memory 43, a timer module 44, a heart rate monitor 45, a display 46, a speaker 47, and a power source 48.

Although illustrated as separate elements, those of skill in the art will recognize that one or more system components may be, or include one or more printed circuit boards (PCB) containing an integrated circuit or circuits for completing the activities described herein. The CPU may be one or more integrated circuits having firmware for causing the circuitry to complete the activities described herein. Of course, any number of other components capable of performing the below described functionality can be provided in place of, or in conjunction with the below described controller elements.

The main body 41 can house each of the elements in a conventional manner, so as to create a single device. In this regard, the main body 41 can preferably be constructed from a thin waterproof material such as lightweight plastic, for example, which can be sewn within the fabric of the suit 10, or removably secured thereon via a tether or other such connector.

The processor/CPU 42 can act to execute program code stored in the memory 43 in order to allow the device to perform the functionality described herein. Likewise, a timer module 44 can be provided, and can function to accurately measure the passage of time. As described herein, the timer module can be provided as a function of the processor or can include a separate physical circuit. In either instance, processors and timers are extremely well known in the art, therefore no further description will be provided.

Memory 43 can act to store operating instructions in the form of program code for the processor 42 to execute. Although illustrated in FIG. 4 as a single component, memory 43 can include one or more physical memory devices such as, for example, local memory and/or one or more bulk storage devices. Additionally, memory 43 can also include one or more cache memories that provide temporary storage of at least some program code in order to reduce the number of times program code must be retrieved from the bulk storage device during execution. Each of these devices is well known in the art.

The Heart Rate Monitor 44 can include a sensor 44a that is in contact with the user's skin at a location that is suitable for detecting the heart rate of the user (e.g., the wrist or chest). When activated, the sensor can detect the user's heart rate, and can send the same to the display unit 46, which can provide the detected heart rate in terms of beats per minute. To this end, the processor can also trigger the speaker to sound an alert in the event that the detected heart rate is above or beneath a user defined threshold.

The visual display unit 46 can include virtually any type of known device capable of presenting information in a digital format to a user via a screen. Several nonlimiting examples include LCD displays, plasma, LED displays, electro-luminescent displays and the like. Additionally, the display unit 46 can also include a Graphic User Interface (GUI) capable of performing two way communication with a device user.

The speaker 47 can function in a conventional manner to play an audible sound such as an alarm tone or a prerecorded message upon being activated by the processor.

In one preferred embodiment, the power source 48 can include one or more DC batteries capable of providing the necessary power requirements to each element of the device 10. The batteries can be permanently located within the main body and can be rechargeable in nature via a charging port such as a mini or micro USB port, for example. Of course, traditional batteries can also be utilized and the main body can further include a battery compartment having a removable cover (not illustrated) for allowing a user to access the same.

In operation, a user can wear the suit during any activity to increase muscle and achieve a greater fitness level. Moreover, the integrated fitness monitor can help the user to achieve their goals, while providing health and safety information to the user at all times.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An exercise suit, comprising:
   a shirt member that is constructed from a single layer of breathable elastomeric material, said shirt member having an inside facing surface an outside facing surface, and a pair of sleeves;
   a pants member having an inside facing surface, an outside facing surface and is constructed from a lightweight breathable and elastomeric material;
   an electronic fitness monitor that is permanently secured onto the shirt member; and
   a plurality of malleable weights, each weight comprising
   a fill material having a specific weight,
   a discrete bag having a surface area that encompasses the fill material, and
   an edging material that is positioned along an outside periphery of the bag, said edging material being sewn directly to the inside facing surface of one of the shirt member and the pants member,
   wherein each of the plurality of malleable weights includes a specific shape and size that is configured to conform to a shape and size of a major muscle group of a human body,
   said plurality of malleable weights comprising
   a single upper back/shoulder weight that is disposed horizontally along a top portion of the shirt member along a back facing side and extending between the pair of sleeves,
   a single chest weight that is disposed horizontally along a top portion of the shirt member along a front facing side and extending between the pair of sleeves, a single abdomen weight that is disposed horizontally along a middle portion of the shirt member and extending between a pair of sides of the shirt member, a single waist weight that is disposed horizontally along an entirety of a bottom end of the shirt member, and a pair of front thigh weights and a pair of rear thigh weights that are disposed along the pants member.

2. The exercise suit of claim 1, wherein the shirt member includes long sleeves, and further comprises a pair of bicep weights, a pair of triceps weights and a pair of wrist weights that are each disposed along an inside facing surface thereof.

3. The exercise suit of claim 1, wherein the pants member includes long sleeves, and further comprises a pair of front calf weights, a pair of rear calf weights and a pair of ankle weights that are each disposed along an inside facing surface thereof.

4. The exercise suit of claim 1, wherein the plurality of weights include a total weight of between 20 and 200 pounds.

5. The exercise suit of claim 1, wherein the shirt member and the pants member are permanently joined together, and further includes a zipper that is disposed along a back end thereof.

6. The exercise suit of claim 1 wherein the electronic fitness monitor further comprises:

a heart rate monitor having a sensor that is positioned along one of the wrist and chest of the suit, said monitor being configured to engage a user's skin to detect a heart rate of the suit user;

a timer that is configured to measure the passage of time; and a display that is configured to show a detected heart rate and a clock.

7. The exercise suit of claim 6, further comprising:

a waterproof main body that is permanently secured to the shirt member, said main body housing the timer and display;

a speaker that is positioned within the waterproof housing;

a memory that is positioned within the waterproof housing; and a processor that is positioned within the waterproof housing, said processor being in communication with each of the memory, speaker, display, timer and heart rate monitor, wherein the electronic fitness monitor includes functionality for generating an audible alarm upon detecting that the detected heart rate of the suit user is above a predetermined threshold.

8. The exercise suit of claim 1, wherein the single upper back/shoulder weight is ten pounds.

9. The exercise suit of claim 1, wherein the single chest weight includes a shape and dimension that is configured to cover an entirety of a suit wearers pictorial muscles.

10. The exercise suit of claim 1, wherein the single chest weight is ten pounds.

11. An exercise suit, consisting of:

a shirt member that is constructed from a single layer of breathable elastomeric material, said shirt member having an inside facing surface, an outside facing surface, and a pair of sleeves;

a pants member having an inside facing surface, an outside facing surface and is constructed from a lightweight breathable and elastomeric material;

an electronic fitness monitor that is permanently secured onto the shirt member; and a plurality of malleable weights, each weight comprising a fill material having a specific weight, a discrete bag having a surface area that encompasses the fill material, and an edging material that is positioned along an outside periphery of the bag, said edging material being sewn directly to the inside facing surface of one of the shirt member and the pants member, wherein each of the plurality of malleable weights includes a specific shape and size that is configured to conform to a shape and size of a major muscle group of a human body, said plurality of malleable weights comprising a single upper back/shoulder weight that is disposed horizontally along a top portion of the shirt member along a back facing side and extending between the pair of sleeves, a single chest weight that is disposed horizontally along a top portion of the shirt member along a front facing side and extending between the pair of sleeves, a single abdomen weight that is disposed horizontally along a middle portion of the shirt member and extending between a pair of sides of the shirt member, a single waist weight that is disposed horizontally along an entirety of a bottom end of the shirt member, and a pair of front thigh weights and a pair of rear thigh weights that are disposed along the pants member.

* * * * *